(12) United States Patent
Hall et al.

(10) Patent No.: US 7,704,750 B2
(45) Date of Patent: Apr. 27, 2010

(54) VISUAL SPILL INDICATOR

(75) Inventors: Richard H. Hall, Midland, MI (US);
Andrew J. Stephenson, Bay City, MI (US)

(73) Assignee: Imbibitive Technologies Corp., Midland, MI (US)

(*) Notice: Subject to any disclaimer, the term of this patent is extended or adjusted under 35 U.S.C. 154(b) by 2040 days.

(21) Appl. No.: 10/311,815

(22) PCT Filed: Jun. 20, 2001

(86) PCT No.: PCT/US01/19779

§ 371 (c)(1),
(2), (4) Date: Dec. 19, 2002

(87) PCT Pub. No.: WO01/98757

PCT Pub. Date: Dec. 27, 2001

(65) Prior Publication Data

US 2008/0108142 A1    May 8, 2008

Related U.S. Application Data

(60) Provisional application No. 60/212,970, filed on Jun. 21, 2000.

(51) Int. Cl.
*G01N 33/18* (2006.01)

(52) U.S. Cl. ............... 436/166; 436/3; 436/169; 422/56; 422/119; 252/190; 252/194; 252/964

(58) Field of Classification Search ............... 436/3, 436/166, 169; 422/56, 119; 252/190, 194, 252/964
See application file for complete search history.

(56) References Cited

U.S. PATENT DOCUMENTS

| 4,313,393 A | 2/1982 | Barbuscio et al. ......... 116/200 |
| 4,822,743 A | 4/1989 | Wegrzyn |
| 5,154,887 A | 10/1992 | Babb et al. |
| 5,270,209 A * | 12/1993 | Rigg et al. ..................... 436/39 |
| 5,342,543 A * | 8/1994 | Morris et al. ............... 252/190 |

(Continued)

FOREIGN PATENT DOCUMENTS

| EP | 0608884 | 8/1994 |
| EP | 1291397 | 3/2003 |
| WO | WO01/98757 | 12/2001 |

OTHER PUBLICATIONS

Web page for Multisorb attributed to Mar. 2, 2000 describing the "DriMop" product.*

(Continued)

*Primary Examiner*—Lyle A Alexander
(74) *Attorney, Agent, or Firm*—Christopher John Rudy (57) ABSTRACT

Composition, which includes a dye that changes color when contacted with a suitable amount of an organic substance, in conjunction with a matrix, paste, support or web, can indicate visually or photometrically the presence of the organic substance. An organic spill absorbing material may be present. For instance, the dye may be selected from the class of anthracene, azo, anthraquinone, pyrazolone, and quinone dyes, and be hydrophobic and organic oleophilic. For an example, the dye may be Oil Red "A." The matrix, paste, support or web may include a microfiber cloth, which may be coated with an adhesive for attachment of the dye, and/or include a water-dissolving paper which may envelope the dye. A device for ascertaining whether an organic substance is present includes the dye or composition with the dye at a certain locale, and a light-transmissive pathway in communication with the location and a detection site external the location. A spectral instrument may be included for the detection, and a remote monitor site may be in communication with the instrument. Various organic substances can be detected, to include oils and gasoline.

26 Claims, 2 Drawing Sheets

U.S. PATENT DOCUMENTS

| | | | |
|---|---|---|---|
| 5,550,061 A | | 8/1996 | Stone |
| 5,788,942 A | * | 8/1998 | Kitani et al. ................... 422/56 |
| 6,162,646 A | * | 12/2000 | Webster et al. .............. 436/166 |
| 6,376,252 B1 | * | 4/2002 | Van Lente et al. ............. 436/66 |
| 6,576,473 B1 | * | 6/2003 | Scaringe et al. ............. 436/169 |
| 6,582,657 B2 | * | 6/2003 | Warner et al. .................. 422/56 |
| 6,905,653 B1 | * | 6/2005 | Higuchi ....................... 422/56 |
| 2005/0196343 A1 | | 9/2005 | Reddy et al. |

OTHER PUBLICATIONS

Search Report, Eur. pat. appl. No. 06394017.5-2204, report issued Dec. 7, 2006 A.D., with annex.

Aftenposten, "Reindeer hair eyed for mopping up oil spills," by Rapp, O.M., www.aftenposten.no, Jan. 30, 2007 A.D., downloaded Feb. 3, 2007.

Patent Database Search Results (ACLM/"slightly crosslinked"); hit list, Feb. 22, 2007.

Patent Database Search Results (ACLM/"slightly cross-linked") hit list, Feb. 22, 2007.

Multisorb Technologies Inc., DriMop® Liquid Absorber, Product information (2 sheets), 2001.

Hall et al., Sep. 4, 2008 Communication (1 sheet) regarding DriMop® Liquid Absorber.

* cited by examiner

VISUAL SPILL INDICATOR

This claims priority of U.S. provisional patent application No. 60/212,970 filed on Jun. 21, 2000. In the U.S.A., benefit of the same is claimed under Section 119(e) of Title 35, U.S. Code.

FIELD

The present invention concerns a composition for indicating visually or photometrically a presence of a contaminant compound or composition, particularly of an organic nature, a device in conjunction with the composition for determining the presence of the contaminant, and a method of use of the composition and/or device. The invention is useful in contaminant detection.

BACKGROUND

There exist many sorption type materials used as wipes, pick up devices for organic spills such as' imbibing polymer bead filled booms, discs and pillows, and so forth, which are used on land and water and underwater installations as well as in portable units in transport including safe shipping containers, on board boats, planes, cars, trucks, and so forth. Many hazardous materials are used which have inhalation, ingestion, and/or body surface contact properties detrimental to people and their safety as well as desirable animal and plant life, and the environment in general, and many of these are organic in nature.

It is unfortunate, however, that, aside from self-indicating materials such as, for example, darkly colored crude oil and dyed fuels, a relatively unmistakable and easy to identify visual indication is unavailable to help one ascertain as to whether or not an organic contaminant may be undesirably present. What is lacking and needed, therefore, is a simple, easy to identify visual type indication that a spill or other release of a contaminating organic substance has taken place or overwhelmed a protective sorbent barrier that has been used as a preventive or prophylactic material or device for containing the contaminant.

SUMMARY

The present invention, in addressing the problems, lacks and needs in the art, provides a composition for indicating visually or photometrically a presence of an organic contaminant compound or composition, said composition comprising a dye, which changes color when contacted with a suitable amount of the organic contaminant, in conjunction with a matrix, paste, support or web. It further provides a device for ascertaining a presence of an organic contaminant comprising a bay in which the aforesaid composition can be located, and a light-transmissive pathway in communication with the bay and a detection site external the bay. It further provides a method for determining a presence of an organic contaminant comprising providing the aforesaid composition to a locus where detection of an organic contaminant is desirable, the composition being provided in an amount effective for indication of the presence of the organic contaminant by change of color of the composition when the composition comes into contact with a suitable amount of the organic contaminant; and checking the composition about the locus to determine if its color has changed.

The invention is useful in contaminant detection.

Significantly, by the invention, the presence or absence of organic contaminants can be checked readily through a readily discernible change of color and light transmission to a detector such as the naked eye or a spectral instrument, which need not be sophisticated, at or near the monitored location itself, with, in the case of the spectral instrument, there being the ability to transmit this information electronically or by other means such as a sonic or visual alarm to a location remote from the monitored location. Avoided is the need to move suspect materials to a laboratory for analysis. Such color change detection can allow for increased personnel safety by alerting the operator or monitor to a hazard from a distance without picking up the suspect material or closely approaching it to smell it. The composition is cost effective, and even a relatively unskilled operator can adequately determine the presence of the organic contaminants under visual conditions. The invention is particularly beneficial when used in conjunction with organic spill absorbing materials, for example, Imbiber Beads (™) product available from Imbibitive Technologies, Inc., provided in blankets, booms, discs, pillows, and so forth.

Numerous further advantages attend the invention.

DRAWINGS

The drawings form part of the present specification. With respect to the drawings, which are not necessarily drawn to scale, the following is briefly noted.

ILLUSTRATIVE DETAIL

The invention can be further understood by the present detail, which may be read in view of the drawings. The same should be taken in an illustrative and not necessarily limiting sense.

In general, the indicator is a type of compound or combination of compounds such as, for instance, two compounds that work in tandem as an indicator, which turn color when contacted with a suitable amount of the contaminant. Herein, a color change can include change in emitted or reflected wavelength of any portion of the spectrum, to include X-ray, UV, visible, IR, and so forth parts of the spectrum; from a colorless state to a colored state and vice versa; a change in intensity of a color; and so forth. More specifically, the indicator may be advantageously selected from the class of anthracene, azo, anthraquinone, pyrazolone, or quinone, and so forth and the like type dyes. Beneficially, the indicator is hydrophobic and organo- or oleophilic, i.e., substantially if not essentially water insoluble but soluble in the organic contaminant of interest, for example, in gasoline or oil. Accordingly, the indicator can be a typical red, yellow or blue and/or black dye such as, for example, one or more of the following compounds:

Typical red dyes (oil-soluble, water-insoluble):

Oil Red "A" (Solvent Red 24), i.e., 1-[[2-methyl-4-(2-methylphenyl)-azophenyl]azo]-2-naphthalenol (CAS #85-83-6):

Also, diazo and monoazo quin(n)aphthalone type compounds.
Typical yellow dyes:
p-Dimethylaminoazobenzene:

Also pyrazolone type compounds.
Typical blue dyes:
Indanthrene Blue "R" (Dark Blue):

Also, monoazoanthraquinono type compounds.
Typical black dyes:
Azo dyes, many proprietary compositions such as LX-6532 "Pylakrome Black," available from Pylam Products Co., Inc., Tempe, Ariz., United States of America (U.S.A.).

The indicator may be formulated into a composition comprising the indicator in conjunction with a matrix, paste, support or web, and so forth and the like. As possible examples of such conjunctives may be mentioned natural and synthetic spun or woven cloths, sheets and threads, to include of animal, vegetable, mineral material, for example, cottons, linens, natural and processed or refined cellulosics, acetates, nylons, rayons, polyesters, polyolefins to include polypropylene, organic microfiber felt, silk, wool, chitin, leather, asbestos, glass, and so forth; inorganic and/or organic creams, pastes and so forth such as used for the skin, as lubricants for mechanical devices, as surface protectants for devices and/or structures; paints; adhesives; polymeric solids and semisolids; waxes; and so forth. A beneficially employed conjunctive to be used with an organic liquid soluble indicator in an aqueous environment to contain the indicator dye before its activation is a water-dissolving paper such as toilet tissue, especially that used for portable toilets or commodes, for example, SeaLand brand rapid dissolving toilet tissue from Taylor Made Grove, or even ordinary, more common toilet tissue, for example, Northern Quilted, Charmin, or Angel Soft brands of household toilet tissue, in which the indicator dye may be enfolded: upon contact with water the paper dissolves, allowing the-dye to be contacted with an organic contaminant, unlike blotting paper which when wet resists penetration of a hydrocarbon contaminant that would otherwise contact the dye and solubilize it, to display its color and indicate the organic contaminant. A sorbent itself, typically employed in conjunction with the indicator and/or matrix, paste, support or web, may serve as the matrix, paste, support or web.

The sorbent may be an adsorbent or an absorbent of the organic contaminant. Preferably, the sorbent is the absorbent. Beneficially, the absorbent is or contains water insoluble, particulate polymer particles which imbibe liquid organic materials. As described in Hall et al., U.S. Pat. No. 3,750,688, on contact with the organic material the absorbent may swell as it is absorbed or imbibed. It may not be critical to employ a cross-linked polymer that swells but does not dissolve. However, cross-linked organic liquid-imbibing polymers are preferred. A wide variety of polymeric materials are employed with benefit. Such polymers include polymers of styrenes and substituted styrenes; copolymers of vinyl chloride including a copolymer of sixty weight percent vinyl chloride and forty weight percent vinyl acetate; vinylidene chloride copolymers including a copolymer of seventy-five percent vinylidene chloride and twenty-five percent acrylonitrile; acrylic polymers such as polymers of methylmethacrylate, ethyl acrylate, and so forth and the like. Particularly advantageous materials which respond to a wide variety of organic liquids are the polymers of styrene such as polystyrene and polymers of styrene and divinylbenzene containing up to ten weight percent divinylbenzene. For general use with aliphatic and aromatic hydrocarbons, alkylstyrene polymers are of particular benefit. When considered for drain or other device shut off systems which employ the imbibing polymers, such alkylstyrene polymers swell very rapidly on contact with aliphatic and/or aromatic hydrocarbons. Generally, the more rapid swelling of the polymer is, the more rapid is the shut off when the organic liquid contaminant is contacted. Alkylstyrene polymers usually show substantial swelling in less than a minute when in contact with organic liquids. Cross-linked polymers of styrenes, notably tertiary-alkylstyrenes, are used to advantage as the imbibing agent. Those alkylstyrenes which can be used to prepare these imbibing polymers have alkyl groups having four to twenty, especially four to twelve, carbon atoms, examples of which include p-tert-, n-tert-, sec-, and/or iso-alkyl styrenes such as of butylstyrene, amlystyrene, hexylstyrene, octylstyrene, dodecylstyrene, octadecylstyrene and eiscosylstyrene. Further, cross-linked copolymers of such alkylstyrenes as aforementioned and an alkyl ester derived from a one to eighteen carbon alcohol and acrylic or methacrylic acid or mixture thereof. Suitable monomers which can be employed as comonomers with the alkylstyrene include such materials as vinylnaphthalene, styrene, alpha-methylstyrene, ring-substituted alpha-methylstyrenes, halostyrenes, arylstyrenes and alkarylstyrenes, methacrylic esters, acrylic esters; esters and half esters of fumaric, maleic, itaconic acids; vinyl biphenyls, vinyl esters of aliphatic carboxylic acid esters, alkyl vinyl ethers, alkyl vinyl ketones, alpha-olefins, iso-olefins, butadiene, isoprene, dimethylbutadiene, acrylobisnitrile, methacrylonitrile, and so forth and the like. A slight amount of cross-linking agent can be contained in the polymer, say, in the range about from 0.01 to two percent by weight. A highly efficient imbibition of organic liquid contaminants occurs when the level of cross-linking agent is less than about one percent by weight since this permits the polymers to swell easily and imbibe a substantial volume of the organic material. When organic liquid-contaminated water is percolated through a packed column or bed of only polymer particles, up to two percent cross-linking agent is satisfactory. Suitable cross-linking agents include polyethylenically unsaturated compounds such as divinylbenzene, diethylene glycol dimethacrylate, diisopropenylbenzene, diisopropenyldiphenyl, diallylmaleate, diallylphthalate, allylacrylateps, allymethacrylates, allylfumarates, allyliltaconates, alkyd resin type cross-linking agents, butadiene or isoprene polymers, cyclooctadiene, methylene norbornlylenes, divinyl phthalates, vinyl isopropenylbenzene, divinyl biphenyl, as well as any other di- or poly-functional compounds known to be of use as a cross-linking agent in polymerical vinyl addition compositions. If there is too much cross-linking agent, the imbibition takes an unreasonably long time, or the polymer is unable to imbibe a sufficient quantity of the organic liquid, and interstitial spaces in the bed are closed. If the imbibitional polymer contains no or too little cross-linking agent, then it may well eventually dissolve or partially dissolve in the organic material resulting, for example, in a non-discrete, non-particulate mass of polymer-thickened organic liquid. However, for many applications where closure of a line is quickly noticeable, uncrosslinked material is satisfactory. The imbibing polymers may be prepared by any suitable technique. For instance, suspension, emulsion or mass polymerization may be employed. Generally, as is well known in the art, the method of preparation is selected to provide imbibing polymer in the most convenient form for any particular application. A latex polymer such as described in Larson et al., U.S. Pat. No. 4,302,337, or other polymer may be employed as the organic liquid imbibant as well.

Amounts of the indicator employed may vary. In general, any suitable amount of the indicator to obtain the desired effect of an appropriate color change may be employed.

Figure 1:
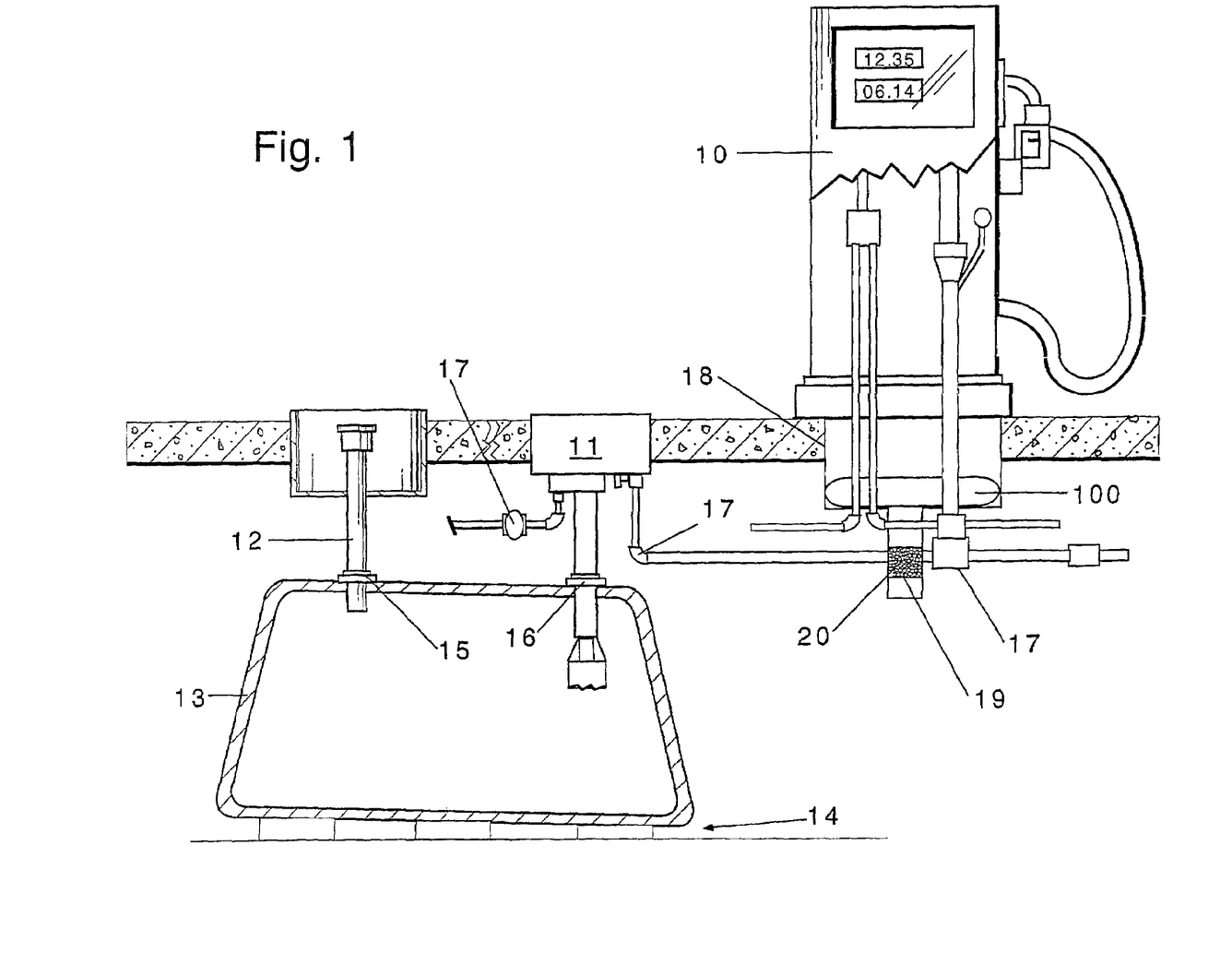
FIG. 1 is a plan view of a device of the invention installed at an illustrative site, a gasoline station, where monitoring for organic contaminants, to include gasoline, is desired.

Further in the practice of the present invention, the following is noted:

The volume beneath a dispenser pump at a service station includes a plethora of pipes and connectors. An inspection port or the side of the unit can be opened, but when it is opened, a white spill indicator unit that had become bright red owing to contamination with gasoline which contacted the indicator gives notice that a spill had taken place, or that perhaps a drip leak had occurred. An absorbent pad unit that could contain, say, up to a gallon of gasoline, would show when a leak had occurred and when the capacity of the device had been exceeded. See, FIG. 1, in which the following features are noted:

| No. | Feature |
|---|---|
| 10 | Gasoline dispenser |
| 11 | Underground gasoline pump |
| 12 | Underground gasoline storage tank fill pipe |
| 13 | Underground, double walled gasoline storage tank |
| 14 | Foundation for storage tank |
| 15 | Underground fill pipe connector to tank |
| 16 | Underground pump tank connector |
| 17 | Other fittings on pipes |
| 18 | Pan under gasoline dispenser |
| 19 | Water drain |
| 20 | Sealing layer |
| 100 | Indicating pad device of the invention. |

The location of the indicator 100 within the device can be spread over the whole device, giving an indication anywhere on the unit that it is touched by an activating spill. The indicator 100 may be located in a small area, for example, a central area, in a more concentrated form, yielding a bright color indication that a spill was reaching the whole unit. This would also be useful for indicating drips under valves, pump packing, instrument attachments, piping connectors, welded joints, and so forth. The indicator 100 can be located at the edge of the unit or even under the surface of the device.

Remote monitoring can be carried out in various ways.

For example, light source 30, say, a spotlight, may shine on the indicator 100, and detector 31, which may be a photodetector, can detect the change in light received as would be reflected from the indicator 100. For instance, the photodetector 31 may be normally off under light conditions, and the indicator 100 may be or contain a white or light colored solid, water insoluble dye that changes to a darker shade or different color when in contact with an organic contaminant; when suitable organic contact occurs, the indicator dye 100 darkens or has its color changed, and the photodetector 31 detects this and transmits its data to remote location 32 for output there, which may be monitored by live personnel and/or computer. See, FIG. 2.

As another example, the light source 30, which may even be ambient light, generates or provides light which is passed through light-transmitting input rod 35 to the indicator 100, with the light pathway completed through light-transmitting output rod 36 which receives and transmits light reflected off the indicator 100. Any discernible shade and/or color change in the indicator 100 upon contact with organic contaminant is detected by the detector 31, which may, for instance, be a photodetector device and/or simply be the naked or optically assisted eye. The reflected light, when activated by dye in the indicator 100 in contact with a suitable organic contaminant, may darken or change color, say, from white or a light color to red or even black, and be detected. See, FIG. 3.

Figure 3:
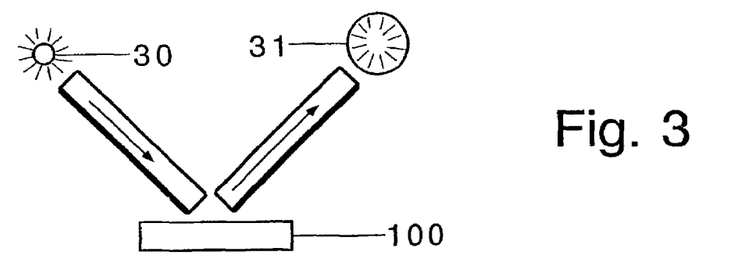
FIG. 3 is a plan view of a visual detector monitoring device of the invention.

Thus, the indicating device 100 can be inside the dispenser pump 10 at a gasoline station, the bilge of a boat or ship, at the bottom of a bulk storage tank base unit, inside a double wall tank 13, under critical storage, piping or valving 14, 15, 16, 17 and so forth—anywhere leaks or spills are likely. If, say, a black colored dye is used in the indicator 100, almost no light from the down light pipe 35 will be reflected up the sensor light pipe 36; accordingly, light colored dyes are preferred. A simple photo cell 31 can be used to signal locally, or even at a remote location 32 miles away. For unmanned service stations, remote tanks, hidden fuel storage, boat bilges, and other locations, this offers simple indication, only if and when product organic is released.

The dye itself of the indicator 100 can be a liquid or solid, but the solid is generally more desirable. In most cases the indicating material should be water insoluble. Most but not all emplacements are contemplated to be in the presence of water. An exception would be in a chemical shipping package where the only material to be spilled and expected to be in the emplacement is a relatively pure organic compound, say, a bottle of hexane or diethylene glycol. If the spilled material is itself a dark brown or black color, like some crude oils, it is visually self indicating. However, even some crude oils can be pale yellow or light tan, and the benefits of indicating the difference between dirty water and a spill of the lightly colored crude with the indicator compound and/or composition, owing particularly to a low flash point of such crude would be well appreciated by those risking their lives to clean up or handle the spill. As well, when sweeping or monitoring a river with booms, say, loaded with the Imbiber Beads material, to prevent or monitor downstream contamination, it is desirable to know where the spill is located in time to deploy additional units, which the indicating ability of the invention can provide. For instance, using different density devices such as indicating unit pads one can monitor an outfall for floating organic material, and with weighted indicator-containing units one can monitor dense non-aqueous phase liquids (DNAPLS) such as chlorinated or brominated organic materials "floating" or moving on the bottom of a river or stream. Such indicating units may be located such that outfall water flows through and around the indicating units and can even be provided to monitor organic compounds having limited water solubility. Thus, responsible users of organic substances can monitor their waters moving offsite with confidence.

Figure 4:
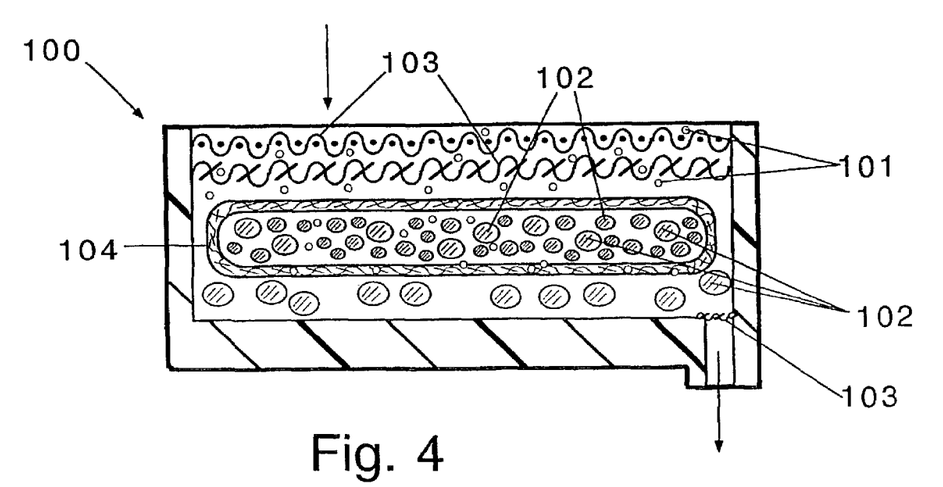
FIG. 4 is a sectional view of an indicator-containing construction of the invention.

Furthermore, the indicator 100 can be solid indicating dye 101 blended into particulate sorbent 102 and then contained in and by outer foraminous cover 103. The indicating material can be loose in the unit if the particle size is larger than the openings in the foraminous cover. Water-soluble paper layer 104 may envelope the dye 101, See, FIG. 4.

Generally in the practice of the invention, although the typical organic contaminant under consideration is considered a liquid, the organic contaminant may be generally considered to be a fluid, to include a gas, a liquid and a supercritical fluid. Thus, it may be possible to monitor methane, propane, butane, butadiene, 2-acrylonitrile and so forth contamination when such volatile organic substances are in their gaseous or liquid form. It is particularly noteworthy that since a liquid form could in general dissolve more noticeably the dye, the liquid form is more prone to ready detection. However, a compound even such as methane can reach liquid temperatures and accordingly be more prone to detection with the indicator of the invention, although it may provide some indication of exposure as a gas.

Furthermore, the term "contaminant" is used herein. However, that which in one case is a contaminant may in other cases simply by an organic compound which can be monitored with the invention. So, the invention can monitor non-contaminant organic substances.

The following embodiments of the invention are noted:

1) compositions to indicate when an organic material that is colorless or neutral (light) in coloring has been picked up by a sorbing device, both absorbent and adsorbent as in ASTM F-716 and F-726 performance standards definitions.

2) A composition that turns from the sorbent color to red, blue, green, yellow, brown and/or black when in contact with an organic compound that by itself has a neutral or light color.

3) A device, which can include the indicator composition, that indicates when a spill has occurred and when spilled product or otherwise monitored product has been sorbed by itself, while in or on water, or underwater.

4) An item that indicates that an organic spill, which is desirably not affected by water but only by the organic material that is picked up by absorbtion or adsorption.

5) An ability to show visually that an organic fluid, spilled or otherwise present, has been absorbed or adsorbed by the significant color change—optionally which makes a relatively easy determination on-site without taking the time to send material for analysis, and further optionally which also allows the visual senses to determine how far a spill has progressed, as well as the ability to know visually that a barricade of sorbent such as a boom has been breached.

6) When a device either white or another color, changes color when contacted with an organic material.

7) When the device changes from white to red, or yellow to orange, or blue to purple, in contact with the organic material.

8) When the device changes from yellow to orange, or yellow to green, in contact with the organic material.

9) When the device changes from blue to purple, in contact with the organic material.

10) When the device changes from colorless or white to red, in contact with an organic material.

11) When the device changes from colorless or white to red, in contact with an organic material, and the color change passes through a filter such that the red color is indicated as a dark brown or black.

12) When the device includes an adsorbent (ASTM F-726) such as melt-blown polypropylene and changes from white or colorless to red, or white or colorless to blue, or white or colorless to yellow, or yellow to green, in contact with the organic material, optionally, the device being a pad, blanket, pillow, boom, or particulate, and the actual use as an adsorbent for an organic material can be followed from a safe distance, optionally the device able to be used on spills or as a packaging cushion, beneficially, knowing when additional sorbent is needed or when an organic breaks through a barrier so that it may be possible to save health, lives, and the environment.

13) When the device includes an absorbent (ASTM F-726) in the form of a pad, blanket, pillow, boom, or particulate, and a significant color change, which may be from white or colorless to red, from yellow to orange, from white or colorless to blue, or from yellow to green, takes place when the organic material spilled or otherwise wets the device.

14) The use of a packaging unit that visually indicates leakage or fracturing of a container with consequent spillage, optionally, in the case of fluid in an absorbent, the change in color staining the carton or when opened indicating even through a clear plastic film or barrier film liner that an accident has occurred.

15) The use of a packaging unit that visually indicates leakage or fracturing of a container, optionally, in the case of an absorbent unit, the change in color indicating visually the presence of a hazard even through a clear plastic film or barrier film liner even though the fluid, preferably a liquid, is contained and resistant to release from the absorbent by squeezing.

16) Visual and photometric spill-monitoring devices, systems, and methods, based on dye color change by organic fluid contact.

17) Employment of one or more dyes in the practice of the present invention such as those selected from the list of types or colors of oil-soluble dyes available from the aforementioned Pylam Products Co., Inc., as follows:

| Type | Number | Specific Color |
| --- | --- | --- |
| Black | LX-1932 | Pylakrome Black |
| | LX-1989B | Pylakrome Fast Black |
| | LX-5745 | Pylakrome Plastic Black |
| | LX-6352 | Pylakrome Black |
| | LX-7828 | Pylakrome Black |
| Blue | LX-1922 | Pylakrome Medium Blue |
| | LX-1971 | Pylakrome Fast Blue |
| | LX-6258 | Pylakrome Bright Blue |
| | LX-6508 | Pylakrome Blue R |
| | LX-6694A | Pylakrome Dark Blue |
| | LX-7329 | Pylam Blue |
| | LX-10287 | Pylakrome Blue Green |
| Brown | LX-1928 | Pylakrome Tan |
| | LX-1929 | Pylakrome Yellow Brown |
| | LX-1930 | Pylakrome Red Brown |
| | LX-1931 | Pylakrome Chocolate Brown |
| | LX-6305A | Pylakrome Dark Brown |
| | LX-6928 | Pylakrome Amber |
| | LX-8149 | Pylakrome Dark Brown |

-continued

| Type | Number | Specific Color |
|---|---|---|
| Green | LX-1915A | Pylakrome Dark Green |
| | LX-1919 | Pylakrome Green |
| | LX-1920 | Pylakrome Fast Blue Green |
| | LX-1993A | Pylakrome Brilliant Green |
| | LX-6679 | Pylakrome Green |
| | LX-6771A | Pylakrome Avocado |
| | LX-6835 | Pylakrome Mint Green |
| | LX-6864 | Pylakrome Bright Green |
| | LX-10509 | Pylakrome Blue Green |
| | LX-10713 | Pylakrome Fluorescent Green |
| Orange | LX-1906A | Pylakrome Apricot Orange |
| | LX-1910A | Pylakrome Reddish Orange |
| | LX-1911A | Pylakrome Orange |
| | LX-5779 | Pylakrome Bright Orange |
| | LX-6692 | Pylakrome Apricot |
| | LX-10093 | Pylakrome Fluorescent Orange |
| | LX-10710 | Pylakrome Orange |
| Red | LX-1900 | Pylakrome Rose Pink |
| | LX-1902 | Pylakrome Maroon |
| | LX-1903 | Pylakrome Red |
| | LX-1904A | Pylakrome Scarlet |
| | LX-1905 | Pylakrome Chinese Scarlet |
| | LX-5988 | Pylakrome Bright Red |
| | LX-9269 | Pylam Oil Red |
| | LX-10096 | Pylakrome Red |
| | LX-10185 | Pylakrome Red |
| | LX-10905 | Pylakrome Dark Magenta |
| | LX-10920 | Pylakrome Dark Red |
| Violet | LX-1926 | Pylakrome Violet |
| | LX-5764 | Pylakrome Lavender |
| | LX-6184 | Pylakrome Purple |
| | LX-6845 | Pylakrome Bright Purple |
| | LX-8183 | Pylakrome Purple |
| | LX-9598 | Pylakrome Red Violet |
| | LX-9993 | Pylakrome Violet Extra Concentrated |
| | LX-10330 | Pylakrome Blue Violet |
| Yellow | LX-1912A | Pylakrome Golden Yellow |
| | LX-1913A | Pylakrome Yellow |
| | LX-5738 | Pylakrome Lemon Yellow |
| | LX-5880 | Pylakrome Oil Fluorescent |
| | LX-6252 | Pylakrome Fluorescent Yellow |
| | LX-6436 | Pylakrome Golden Yellow |
| | LX-7410 | Pylam Yellow |
| | LX-8248 | Pylakrome Oil Fluorescent Yellow |
| | LX-9563 | Pylakrome Yellow |
| | LX-10140 | Pylakrome Yellow |
| | LX-10684 | Pylakrome Golden Yellow |
| Wood Shades | LX-1940A | Pylakrome Red Mahogany |
| | LX-1941A | Pylakrome Dark Red Mahogany |
| | LX-1942A | Pylakrome Mahogany |
| | LX-1943A | Pylakrome Brown Mahogany |
| | LX-1946 | Pylakrome Walnut |
| | LX-1948 | Pylakrome Dark Walnut |
| | LX-1950 | Pylakrome Maple |
| | LX-1952 | Pylakrome Antique Maple |
| | LX-1954 | Pylakrome Yellow Oak |
| | LX-1955 | Pylakrome Oak |
| | LX-5693 | Pylakrome Medium Walnut |
| | LX-6275A | Pylakrome Cherry Wood. |

The following examples further illustrate the invention:

EXAMPLE 1

An adsorbent polypropylene non-woven pad is separated into thin layers, i.e., 1-2 mm, in the form of a pouch. A small amount of Oil Red A is blown or sprinkled into the cavity. The open edge of this thin assembly is then sealed. Thus, the Oil Red A is prevented from contacting the foraminous surface material, and from turning it "colored" over a period of time. The thickness of the fine fiber assembly yields a depth from the surface that hides the dark red (almost black) color of the Oil Red A.

EXAMPLE 2

A pelletized particle of compacted solid dye is placed next to a film surface or a foraminous surface layer. This pellet product is physically separated from the pad by being inserted into a fiber material that keeps the pellet from fracturing or from staining the foraminous or film surface prematurely.

EXAMPLE 3

A water-based material such as stripped latex, methylcellulose, diluted white glue such as Elmer's glue, white carpenter's glue, etc., can be coated on an organic microfiber felt or plastic fiber material. The organic, water insoluble dye can be suspended and stirred into these thick liquids prior to their use as a coating. When organic contaminant contacts them, they change and show color or show a different color. Such coated materials can be folded and sealed to contain the indicator as well as be tack glued to a foraminous or film surface.

EXAMPLE 4

The coating material from Example 3 can be diluted an sprayed onto a fill, absorbent or adsorbent material(s). When dried, it can be activated and generate a color change when contacted with a spilled organic contaminant or a desired organic compound. Since the indicator agent is evenly distributed, the intensity of color is greater for the same amount of indicator dye if it is closer to the foraminous or film surface.

EXAMPLE 5

A spill pick up material such as Imbiber Beads (™) product is an absorbent for organic substances that prevents color wash off in a flowing spill. On the other hand, adsorbents would engender color wash off of indicator in a flowing spill.

EXAMPLE 6

The indicating pad of Example(s) 1-4 is used separately from the pick up pad to colorize an organic spill. It may also break through product visually.

EXAMPLE 7

As indicated in FIG. 1, an indicating pad 100 can be located under the dispenser island of a gasoline station dispenser 10, in its underground pump catch 11, in the area of the fill pipe 12 near the ground surface, inside the double wall of the double-walled tank 13, or even on the slab on which the tank sets at its lowest point where a spill would run 14. The indicator pad at the fill pipe or dispenser pump can be monitored visually. Other locations can be monitored manually or remotely by using a device such as follows made practical by the color spill indicator unit.

Figure 2:
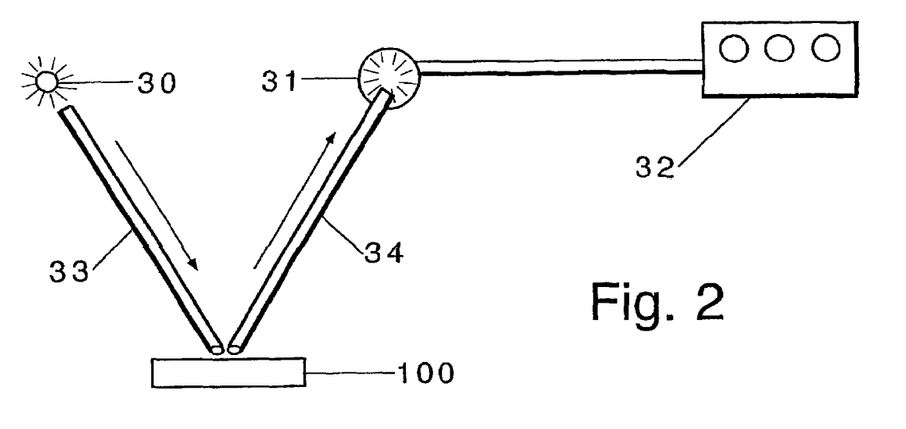
FIG. 2 is a plan view of a photodetector monitoring device of the invention.

As indicated in FIG. 2, light from light source 30 may take a path through a first light pathway 33 to an indicator pad 100 and from there through a second light pathway 34 to a detector 31. The detector 31 may be in communication with an output device or monitor 32 at a remote location.

As indicated in FIG. 3, a set of light pipes 35, 36 such as of glass or polymethamethacrylate rods, or optical fibers, can permit passage of light therethrough. The first pipe 35 can run from the light source 30 to the indicator pad 100, from outside the vapor hazard area. A second separate or coaxial light pipe such as the light pipe 36 can carry reflected light to a detector 31 site, with monitoring, say, by a photodetector or the naked eye. The photodetector can be as simple as a simple photocell such as commonly used in night lights. If a red dye is used, the visual on the reading light pipe changes from the original color, say, white, to the contaminant-indicating color, red. A visual indication of a spill will thus be readily visible and detectable by even operators of little skill. If a filter for the red light is used, the contaminant-indicating color may appear to be black, which also is very vivid in comparison to white and can serve as the control activation for the photocell, and if a black color is used, the visual difference will be from light to dark, which is a very easy control for the photocell or for visual monitoring. Nonetheless, a vivid color such as red, or even, say, orange, may signify to the manual operator a rather dramatic visual indication of danger owing to an organic spill.

Furthermore, such types of devices and techniques can readily modified to be used to monitor the bilge of a boat or ship, an unloading platform, or the outfall of a separator that has been overwhelmed or upset. The ability to monitor pumps, sumps, valve and other connections in piping, bays, holds, places between walls, places behind or under storage tanks, and so forth by such a simple system as of the invention, not dependent on anything but the product being monitored, is of inestimable value. What is more, since monitoring can be carried out from a distance from the site of the spill or potential for a spill, the safety of personnel can be improved greatly from the old "go and sniff" command from a supervisor. Moreover, the ability to protect the environment is an advantage that would benefit many an operating site.

EXAMPLE 8

A pad is prepared by splitting the layers of an adsorbent pad of non-woven, melt-blown polypropylene microfibers with an about 0.3175-centimeter (cm) thickness. The weight of an about 15.24-cm by 15.24-cm pad fiber square is 4-5 grams (g). In the middle of the pad fiber is sprinkled 0.005-0.1 g of solid Oil Red A dye over a central about 10.16-cm by 10.16-cm area. A second about 0.3175-cm thick piece pad is placed on top of the one having the dye sprinkled thereon, and the pads are sealed at the edge. The seal can be a melt-heat seal, stitching, water-resistant exterior wood glue, taping, and so forth. This pad is placed inside an absorbent pad near the surface of its containment fabric. It can be tacked to the surface by stitching, gluing with a water-based wood glue, taping, and so forth, or heat-sealed into the pad. When placed in water, the pad maintains its natural color, commonly white. When contacted by gasoline, diesel fuel or other organic fluid that dissolves the solid dye, the pad surface turns a bright red.

By visual observation or other optic means such as through photodetection, it becomes apparent that an organic material it present in the pad. The system also works if no water is present, as would be the case inside a gasoline dispenser pump under the piping and connections leading to the meter and pump dispensing nozzle system.

EXAMPLE 9

An about 15.24-cm by 15.24-cm piece of organic microfiber felt pad (4-5 g) is covered in a central about 10.16-cm by 10.16-cm square with 0.05-0.1 g of a solid, water insoluble, oil soluble dye such as an azo dye, Black LX-6352 dye. A second piece of the organic microfiber felt pad is placed over this, enclosing the solid dye. This unit is sealed inside an adsorbent pad of melt-blown polypropylene microfiber meeting ASTM F-726 or an absorbent pad meeting ASTM F-716 performance standards. When contacted with an activating organic substance that dissolves the dye, what has typically been a white material turns black, visually indicating the presence of the organic, either dry or wet with water.

An additional advantage of this type of system is the ability to project a cold light onto this contrivance by means of a light pipe. The reflected light can then be seen through a similar light pipe. In addition to or in lieu of a visual sighting, such drastic change in the amount of reflected light can be used to activate a photocell similar to the well known and widely used "nite lite." The light reflected off a white unit will keep the system off, just as light on the "nite lite" photocell keeps the light bulb off. But when the light from the light pipe carrying reflected light from the activated color pad becomes a much reduced light, then the unit is activated, akin to the situation in the "nite lite" where its bulb is lit. Such a unit has great value in remote locations to include in such locations as unmanned power stations or automated, unmanned service stations, as well as having practical application in boat bilges, or for responsible caring companies monitoring their facilities or waste systems. Compare, FIGS. 2 and 3.

EXAMPLE 10

An about 15.24-cm by 15.24-cm piece of organic microfiber felt pad about 4.5 g in weight is coated with an aqueous glue like Elmer's white glue. Approximately 0.1 g of solid Oil Red A powder is sprinkled on an about 10.16-cm by 10.16-cm square of the felt. A piece of heat-fused polypropylene nonwoven fabric is heat sealed onto and/or around this pad to prevent washing away of the felt. When used by itself or in a pad of adsorbent or absorbent material, this device visually indicates contact with a typical organic such as gasoline, but, of course, not limited to gasoline.

EXAMPLE 11

A piece of blotting paper is treated as in Examples 8, 9 and 10. When the blotting paper is wet with water first, it keeps gasoline from making the dramatic color change.

EXAMPLE 12

An organic dye (Oil Red A or Pylakrome Black, LX-6532) was melted and then ultimately broken up into chunks. The reduced surface area material took much longer to develop significant color than powder of the corresponding material.

EXAMPLE 13

The organic dye of Example 12 was deposited on a high surface area solid of an adsorbent mat of polypropylene microfiber. Best results were obtained when the dye powder, particles or pellets were shielded by an about 0.3175-cm sheet of microfiber. This kept a colored tinge from forming on an outer fabric layer. It was possible to spray the microfiber with an organic (rubber type) spray adhesive that would hold the powder inside two pieces of microfiber and repel water, yet develop rapid color when contacted by an organic, water insoluble fluid.

EXAMPLE 14

The dye of Example 12 was dissolved in solvent, which developed intense color. A high surface area polypropylene microfiber or a fine cell macroreticular urethane foam was placed in the liquid solution, and the solvent was dried to provide an indicator pad.

EXAMPLE 15

The procedure of Example 14 also works if it is used inside an untreated polypropylene microfiber pad to shield the color development until activated. The working and moving of the dye-coated material causes a flaking and fracturing of the dye coating. A soluble hot melt glue or a rubber cement introduced in the solvent for the dye gave a dye product that adhered to the substrate, and if adequate rubber cement was used, it gave a dye product having a much reduced tendency to fracture. This combination yields a high surface area dye indicator that has resistance to fracturing and dusting, with rapid color development.

EXAMPLE 16

An organic wick used with absorbent bead product packets is sprayed with a rubber adhesive. Dye of Example 12, powdered, is then dusted on the wick when the solvent from the spray evaporated. This gives a high surface area base for rapid color development when contacted with an organic compound.

EXAMPLE 17

A high surface area substrate is coated with a water-soluble adhesive such as Elmer's school glue. When the water for the most part is evaporated, the powdered dye of Example 16 is dusted onto the surface of the substrate. When contacted with an organic that activates the dye, the color formation is rapid and easily seen.

EXAMPLE 18

When used in a boat bilge, an indicating dye is advantageously used that is decolorized by an oxidizing agent such as household bleach. This will allow a polyester boat bilge to be cleaned and decolorized after a fuel spill has activated an indicating packet.

EXAMPLE 19

The use of a blotting paper to seal in an organic soluble dye does not work as would be desired in all circumstances because the wet layer of the paper resists the hydrocarbon (water-insoluble) material from penetrating the blotting paper to solubilize and release the color indicating the presence of the organic substance. However, paper such as that recommended as a toilet tissue—especially that used for Porta-potties such as SeaLand brand of rapid dissolving toilet tissue (Taylor Made Grove); and even regular toilet tissue such as Northern Quilted, Charmin, or Angel Soft brands—breaks down in water to allow the dye to contact the organic of interest and release the indicating color.

CONCLUSION

The present invention is thus provided. Various features, parts, subcombinations and combinations can be practiced with or without reference to other features, parts, subcombinations or combinations of the in the practice of the invention, and numerous adaptations and modifications can be effected within its spirit, the literal claim scope of which is as follows:

What is claimed is:

1. A composition for indicating visually or photometrically a presence of a substantially hydrophobic fluid organic substance and absorbing or imbibing said substance when present, said composition comprising, in combination:
   a hydrophobic, and organophilic or oleophilic dye, which shows, develops or releases a color with said substance when contacted with a suitable amount of said substance, from activity consisting essentially of dissolving of the dye in said substance, and not from contact with water; in conjunction with a matrix, paste, support or web; and
   a fluid organic spill absorbing material, which contains water insoluble, particulate organic polymer particles that, when contacted with said substance, imbibe said substance and swell substantially upon imbibing said substance or other substantially hydrophobic liquid organic materials absorbable by said particles,
   wherein said dye is provided external said particles.

2. The composition of claim 1, wherein the liquid organic spill absorbing material includes a polymeric bead absorbent that includes an alkylstyrene that is crosslinked, and that, upon squeezing, resists release of any of said substance that is absorbed; and said substance is a liquid.

3. The composition of claim 1, wherein at least one of the following is present:
   a water-dissolving paper, which envelopes at least some of the dye, and/or a microfiber cloth;
   a device useful for ascertaining a presence of a said substance, which includes a bay at a location at which is located said composition; and means for providing a light-transmissive pathway in communication with the location and a detection site external the bay location, which means includes a first, constructed, light-incoming pathway to the bay through which light from a light source can be directed and pass to be targeted onto said composition; the light source; and a second, constructed, light-outgoing pathway for directing reflected light from said composition away from the bay to the detection site;
   a container having an outer foraminous cover through which said substance can pass to come into contact with said composition and material, which container contains said composition and material inside when said substance is passed the therethrough;
   a blanket, pillow and/or a boom useful for absorbing said substance in an environment in which liquid water is present and may be contaminated by said substance, loaded with said material, wherein said dye in said conjunction with the matrix, paste, support or web is in conjunction with said blanket, pillow and/or boom;
   a hollow packaging unit for carrying inside thereof a container having therein said substance, wherein said substance is a liquid, which container may accidentally leak or fracture to release said substance, and wherein:
      said unit carries inside thereof the container having said substance; has an outside window to observe the inside of said unit; and has said material inside said unit, wherein said material includes a crosslinked alkylstyrene that, upon squeezing, resists release of any of said substance that is absorbed;
      said dye in conjunction with the matrix, paste, support or web is in conjunction with at least one of said unit and said material so that a presence of said substance spilled outside said container can be indicated visually or photometrically; and said dye is selected from at least one of the class of anthracene, azo, anthraquinone, pyrazolone, and quinone dyes.

4. The composition of claim 1, wherein the dye is selected from at least one member of the group consisting of a red, yellow, blue and black dye.

5. A composition for indicating visually or photometrically a presence of a fluid organic substance, said composition comprising a hydrophobic, and organophilic or oleophilic dye, which shows, develops or releases a color with said substance when contacted with a suitable amount of said substance, from activity consisting essentially of dissolving of the dye in said substance, and not from contact with water; in conjunction with a matrix, paste, support or web; wherein:
   a fluid organic spill absorbing material is present, which contains water insoluble, particulate organic polymer particles that can imbibe liquid organic materials; and
   the matrix, paste, support or web includes at least one of the following:
      a water-dissolving paper, which envelopes at least some of the dye; and
      a microfiber cloth.

6. The composition of claim 5, wherein the matrix, support or web includes the microfiber cloth; said substance is a liquid, and said material is a liquid organic spill absorbing material.

7. The composition of claim 6, wherein the microfiber cloth is coated at least in part with an adhesive, and at least some of the dye is attached thereto.

8. The composition of claim 5, wherein the matrix, paste, support or web includes the water-dissolving paper which envelopes at least some of the dye.

9. The composition of claim 8, wherein the dye is hydrophobic, and organophilic or oleophilic; said substance is a liquid, and said material is a liquid organic spill absorbing material, which includes a polymeric bead absorbent.

10. The composition of claim 9, wherein the polymeric bead absorbent includes water insoluble, particulate particles, which imbibe liquid organic materials and which are made of a cross-linked organic liquid-imbibing polymer.

11. A device useful for ascertaining a presence of a fluid organic substance comprising:
   a bay at a location at which is located a composition for indicating visually or photometrically a presence of said substance, said composition including a hydrophobic, and organophilic or oleophilic dye, which shows, develops or releases a color with said substance when contacted with a suitable amount of said substance, from activity consisting essentially of dissolving of the dye in said substance, and not from contact with water; in conjunction with a matrix, paste, support or web; wherein:
      a fluid organic spill absorbing material is present, which contains water insoluble, particulate organic polymer particles that can imbibe liquid organic material, materials; and
      said dye is external said particles; and
   means for providing a light-transmissive pathway in communication with the location and a detection site external the bay location, wherein the means for providing the light-transmissive pathway includes the following:
      a first, constructed, light-incoming pathway to the bay through which light from a light source can be directed and pass to be targeted onto said composition;
      the light source; and
      a second, constructed, light-outgoing pathway for directing reflected light from said composition away from the bay to the detection site.

12. The device of claim 11, wherein the light source includes light from other than ambient light, and said first and second pathways are formed by solid, light-transmissive material (s).

13. The device of claim 11, wherein the detection site includes a spectral instrument, and a remote monitor site in communication with the spectral instrument is present.

14. In combination, a composition for indicating visually or photometrically a presence of a liquid organic substance, said composition comprising a hydrophobic, and organophilic or oleophilic dye, which shows, develops or releases a color with said substance when contacted with a suitable amount of said substance, from activity consisting essentially of dissolving of the dye in said substance, and not from contact with water; in conjunction with a matrix, paste, support or web; wherein:
   a liquid organic spill absorbing material is present; and
   a container having an outer foraminous cover through which said substance can pass to come into contact with said composition and material, which container contains said composition and material inside when said substance is passed therethrough.

15. The combination of claim 14, wherein the dye is a solid, and is blended with but provided external to particles of a particulate sorbent.

16. The combination of claim 15, wherein at least part of the liquid organic spill absorbing material and the particulate sorbent are the same and include a polymeric bead absorbent.

17. The combination of claim 15, wherein water-soluble paper envelopes the dye.

18. The combination of claim 16, wherein water-soluble paper envelopes the dye.

19. The combination of claim 14, wherein the outer foraminous cover includes top and bottom foraminous members with openings thereto.

20. In a device useful for absorbing or adsorbing a generally hydrophobic liquid organic substance in an environment in which liquid water is present and may be contaminated by said substance, said device selected from the group consisting of a blanket, a pillow and a boom, which device is loaded with an absorbent of an organic spill absorbing material, which material contains water insoluble, particulate organic polymer particles that can imbibe said substance, the improvement comprising a hydrophobic, and organophilic or oleophilic dye, which shows, develops or releases a color with said substance when contacted with a suitable amount of said substance, from activity consisting essentially of dissolving of the dye in said substance, and not from contact with water; so that a presence of said substance, when contacted with said device, is indicated visually or photometrically in or on the device.

21. The improvement of claim 20, which is in the form of the boom.

22. The improvement of claim 21, wherein the liquid organic spill absorbing material includes a polymeric bead absorbent that includes an alkylstyrene that is crosslinked, that swells substantially upon imbibing said substance or other substantially hydrophobic liquid organic materials absorbable by said bead absorbent, and that, upon squeezing, resists release of any of said substance that is absorbed.

23. The improvement of claim 20, which further includes an adsorbent, which is of polypropylene.

24. In a hollow packaging unit for carrying inside thereof a container having therein an organic liquid substance, which container may accidentally leak or fracture to release said substance, wherein the hollow packaging unit carries inside thereof the container having said substance, the improvement comprising:
- an outside window to observe the inside of the hollow unit;
- a liquid organic spill absorbing material inside the unit, which material includes a polymeric bead absorbent that includes a crosslinked alkylstyrene and that, upon squeezing, resists release of any of said substance that is absorbed; and
- a hydrophobic, and organophilic or oleophilic dye in conjunction with a matrix, paste, support or web in conjunction with at least one of the hollow unit carrying inside thereof the container having said substance, and the liquid organic spill absorbing material inside the unit; which dye shows, develops or releases a color with said substance when contacted with a suitable amount of said substance, from activity consisting essentially of dissolving of the dye in said substance, and not from contact with water; so that a presence of said substance spilled outside the container can be indicated visually or photometrically.

25. A composition for indicating visually or photometrically a presence of a fluid organic substance, said composition comprising a hydrophobic, and organophilic or oleophilic dye, which shows, develops or releases a color with said substance when contacted with a suitable amount of said substance, from activity consisting essentially of dissolving of the dye in said substance, and not from contact with water; in conjunction with a matrix, paste, support or web; wherein:
- a fluid organic spill absorbing material is present, which contains water insoluble, particulate organic polymer particles that can imbibe liquid organic materials;
- the dye is external said particles; and
- the dye is selected from at least one of the class of anthracene, azo, anthraquinone, pyrazolone, and quinone dyes.

26. The composition of claim 25, wherein the dye is selected from the group consisting of 1-[[2-methyl-4-(2methylphenyl)-azophenyl]azo]-2-naphthalenol;
- p-dimethylaminoazobenzene; indanthrene blue R, and a Pylakrome black.

* * * * *